United States Patent
Kusuda et al.

(10) Patent No.: US 10,344,342 B2
(45) Date of Patent: Jul. 9, 2019

(54) METHOD OF AND APPARATUS FOR PRODUCING SACCHARIFIED SOLUTION BY USING BIOMASS AS RAW MATERIAL, AND CONTINUOUS REACTOR

(71) Applicant: KAWASAKI JUKOGYO KABUSHIKI KAISHA, Kobe-shi, Hyogo (JP)

(72) Inventors: Hiromasa Kusuda, Kobe (JP); Noriaki Izumi, Kobe (JP); Hironori Tajiri, Kobe (JP); Shoji Tsujita, Itami (JP); Masaki Tsuzawa, Kobe (JP)

(73) Assignee: KAWASAKI JUKOGYO KABUSHIKI KAISHA, Kobe-Shi (JP)

( * ) Notice: Subject to any disclaimer, the term of this patent is extended or adjusted under 35 U.S.C. 154(b) by 312 days.

(21) Appl. No.: 15/104,356

(22) PCT Filed: Dec. 19, 2014

(86) PCT No.: PCT/JP2014/006348
§ 371 (c)(1),
(2) Date: Jun. 14, 2016

(87) PCT Pub. No.: WO2015/098070
PCT Pub. Date: Jul. 2, 2015

(65) Prior Publication Data
US 2016/0312319 A1  Oct. 27, 2016

(30) Foreign Application Priority Data
Dec. 26, 2013 (JP) .................................. 2013-269373
Aug. 7, 2014 (JP) .................................. 2014-161541

(51) Int. Cl.
C13K 1/02 (2006.01)
B09B 3/00 (2006.01)
B01J 19/18 (2006.01)
B01F 7/00 (2006.01)

(52) U.S. Cl.
CPC ............ *C13K 1/02* (2013.01); *B01F 7/00291* (2013.01); *B01F 7/00391* (2013.01); *B01J 19/18* (2013.01);
(Continued)

(58) Field of Classification Search
CPC ... C13K 1/02; C13K 1/04; C13K 1/06; C13K 1/08; C13K 13/007; B01J 19/18;
(Continued)

(56) References Cited

U.S. PATENT DOCUMENTS 5,634,715 A  6/1997  Stehr et al.
6,022,137 A  2/2000  White et al.
(Continued)

FOREIGN PATENT DOCUMENTS

CN   2669967 Y   1/2005
CN   103052714 A   4/2013
(Continued)

OTHER PUBLICATIONS

Jun. 26, 2017 Office Action issued in Chinese Patent Application No. 201410792327.7.
(Continued)

*Primary Examiner* — Joseph W Drodge
(74) *Attorney, Agent, or Firm* — Oliff PLC (57) ABSTRACT

A method of producing a saccharified solution, in which saccharified slurry is obtained by hydrothermally treating cellulosic biomass slurry in a supercritical state or a subcritical state by a continuous reactor. The method reduces the risk of a pressure reducing valve becoming clogged when the high-temperature and high-pressure slurry is flash-evaporated after being hydrothermally treated. Also provides an apparatus for producing a saccharified solution and a continuous reactor. At the time of hydrothermally treating the cellulosic biomass slurry by the continuous reactor
(Continued)

continuously, the slurry is intensely stirred in a front part of the continuous reactor, and stirred in a rear part of the continuous reactor by a stirring device with low propelling force, such that the plug flow in the axial direction is kept while the slurry is being uniformly mixed with respect to the cross section perpendicular to the mixing axis.

9 Claims, 5 Drawing Sheets (52) U.S. Cl.
CPC .............. *B09B 3/00* (2013.01); *B09B 3/0091* (2013.01); *Y02E 50/16* (2013.01)
(58) Field of Classification Search
CPC .............. B01J 19/20; B01J 2219/00033; B01J 2219/00481; B01J 2219/00905; B01J 2219/00909; B01J 3/00; B01J 3/0006; B01J 3/0008; B09B 3/0091; B09B 3/00; Y02E 50/16; B01F 7/00233; B01F 7/00291; B01F 7/00308; B01F 7/00391; B01F 7/00416; B01F 7/0045; B01F 7/04; B01F 7/08; B01F 7/085; B01F 7/088; B01F 7/18; B01F 7/24; B01F 7/241; B01F 7/242; D21C 1/00; D21C 1/02; D21C 3/24; D21C 3/26; D21C 5/00; B01D 1/00; B01D 21/00
USPC ..... 127/1, 2, 9, 36, 37, 42, 46.1, 53, 55, 57; 159/22, 29, 47.1; 162/1, 53, 201, 232, 162/381; 210/177, 178, 179, 182, 259, 210/774, 804, 806; 536/127, 128
See application file for complete search history.

(56) References Cited

U.S. PATENT DOCUMENTS

| | | | | |
|---|---|---|---|---|
| 9,850,551 | B2* | 12/2017 | Kusuda | C13K 1/02 |
| 2010/0041119 | A1* | 2/2010 | Christensen | D21C 9/18 |
| | | | | 435/162 |
| 2010/0269990 | A1* | 10/2010 | Dottori | C08H 8/00 |
| | | | | 162/21 |
| 2010/0317053 | A1* | 12/2010 | Stromberg | B01F 7/00766 |
| | | | | 435/41 |
| 2011/0081689 | A1* | 4/2011 | Flanegan | C12P 7/10 |
| | | | | 435/105 |
| 2011/0262985 | A1* | 10/2011 | Medoff | C12P 19/14 |
| | | | | 435/165 |
| 2012/0052543 | A1* | 3/2012 | Yoon | C12P 7/10 |
| | | | | 435/165 |
| 2012/0291774 | A1 | 11/2012 | Kilambi et al. | |
| 2014/0030524 | A1* | 1/2014 | Kadam | C08H 6/00 |
| | | | | 428/402 |
| 2016/0201102 | A1* | 7/2016 | Zhu | C12P 19/02 |
| | | | | 435/68.1 |

FOREIGN PATENT DOCUMENTS

| | | |
|---|---|---|
| JP | 2000-186102 A | 7/2000 |
| JP | 2002-059118 A | 2/2002 |
| JP | 2003-212888 A | 7/2003 |
| JP | 2006-068606 A | 3/2006 |
| JP | 2010-081855 A | 4/2010 |
| JP | 2012-000022 A | 1/2012 |
| JP | 2013-165719 A | 8/2013 |
| JP | 5600203 B1 | 10/2014 |
| KR | 2012 0088096 A | 8/2012 |
| WO | 2008/050740 A1 | 5/2008 |
| WO | 2012/167789 A2 | 12/2012 |
| WO | 2013/046622 A1 | 4/2013 |

OTHER PUBLICATIONS

Oct. 20, 2017 Office Action issued in Australian Patent Application No. 2017203196.
Feb. 3, 2015 International Search Report issued in International Patent Application No. PCT/JP2014/006348.
Feb. 3, 2015 Written Opinion issued in International Patent Application No. PCT/JP2014/006348.

* cited by examiner

METHOD OF AND APPARATUS FOR PRODUCING SACCHARIFIED SOLUTION BY USING BIOMASS AS RAW MATERIAL, AND CONTINUOUS REACTOR

TECHNICAL FIELD

The present invention relates to a method of and an apparatus for producing a saccharified solution by hydrolyzing cellulosic biomass in a supercritical state or a subcritical state. The method and apparatus utilize saccharides to produce a biochemical such as ethanol (bioethanol) or polylactic acid by fermentation such as alcoholic fermentation or lactic acid fermentation. The present invention also relates to a continuous reactor suitable for use in the apparatus that produces a saccharified solution by hydrolyzing cellulosic biomass in a supercritical state or a subcritical state.

BACKGROUND ART

As part of biomass energy utilization, attempts have been made to hydrolyze cellulose or hemicellulose, which are major components of plants, to produce a saccharified solution, and then obtain ethanol from the saccharified solution through alcoholic fermentation of sugar. Ethanol thus obtained is planned to be utilized mainly as a fuel to be mixed into an automobile fuel or as an alternative fuel for gasoline.

In recent years, industrially, a saccharified solution obtained by hydrolytically saccharifying cellulose or hemicellulose is used for lactic acid fermentation to produce L-lactic acid, which is then polymerized to produce polylactic acid, which is one kind of biomass-based polymer. Polylactic acid has been drawing attention as a biodegradable plastic.

Major components of plants include cellulose (a polymer of glucose which is a C6 monosaccharide composed of six carbon atoms), hemicellulose (a polymer of C5 and C6 monosaccharides; a C5 monosaccharide is composed of five carbon atoms), lignin, and starch. Ethanol is produced by using saccharides as raw materials, such as a C5 monosaccharide, a C6 monosaccharide, and an oligosaccharide which is a complex of these saccharides. Ethanol is produced through fermentation of microorganisms such as yeast.

For hydrolyzing cellulosic biomass containing cellulose or hemicellulose into saccharides, there are the following three possible methods to be industrially applied: 1) a method of hydrolyzing such biomass by utilizing oxidizing power of a strong acid such as sulfuric acid; 2) a method of hydrolyzing such biomass by utilizing an enzyme; and 3) a method utilizing oxidizing power of supercritical water or subcritical water. However, the acidolysis method 1) indispensably requires a treatment for neutralizing the added acid after hydrolysis of cellulose or hemicellulose into saccharides and before fermentation of the saccharides, because the added acid acts as an inhibitor against fermentation bacteria, such as yeast or lactic acid bacteria. The cost of such treatment makes it difficult to put this method into practical use from an economic standpoint. Although the enzymolysis method 2) can be realized by a treatment under a normal temperature and constant pressure, no effective enzyme for the method has been found yet, and even if an effective enzyme is found, the outlook for industrial-scale realization of the method is still unclear in terms of cost efficiency, because such an enzyme is expected to incur a high production cost thereof.

As examples of the method 3) of hydrolyzing cellulosic biomass into saccharides by using supercritical water or subcritical water, there are disclosed methods as described below. Patent Literature 1 discloses a method of producing water-insoluble polysaccharides, which is characterized by hydrolysis of cellulose powder that is performed by bringing the powder into contact with pressurized hot water of 240 to 340° C. Patent Literature 2 discloses a method including: hydrolyzing biomass chips for a predetermined time with hot water pressurized to a saturated vapor pressure or higher at 140 to 230° C., thereby extracting hemicellulose; and then hydrolyzing the biomass chips with pressurized hot water heated to a temperature not lower than a cellulose hydrolyzing temperature, thereby extracting cellulose. Patent Literature 3 discloses a method of producing glucose and/or water-soluble cello-oligosaccharides, which is characterized in that cellulose with a mean polymerization degree of not less than 100 is hydrolyzed by: bringing the cellulose into contact reaction with supercritical water or subcritical water at a temperature of not lower than 250° C. and not higher than 450° C. and at a pressure of not lower than 15 MPa and not higher than 450 MPa for a time period of not less than 0.01 second and not more than 5 seconds; then cooling down the cellulose; and thereafter bringing the cellulose into contact with subcritical water at a temperature of not lower than 250° C. and not higher than 350° C. and at a pressure of not lower than 15 MPa and not higher than 450 MPa for a time period of not less than 1 second and not more than 10 minutes.

Patent Literature 4 discloses a method of producing saccharides, by which not only are the saccharides obtained from ligneous biomass with high yield and high efficiency, but also saccharides containing C5 and C6 saccharides and saccharides containing C6 saccharides can be separately collected. The method of producing saccharides disclosed in Patent Literature 4 includes: a first slurry heating step (S1) of heat-treating slurry that is prepared by adding high-temperature and high-pressure water to ligneous biomass; a first separating step (S2) of separating the heat-treated slurry into a liquid component and a solid component; a second slurry heating step (S3) of adding water to the separated solid component to form slurry and heat-treating the slurry; a second separating step (S4) of separating the heat-treated slurry into a liquid component and a solid component; and a useful component obtaining step (S5) of removing water from the separated liquid component to obtain saccharides. The method is characterized by obtaining saccharides by removing water from the liquid component separated in the first separating step (S2) in addition to obtaining saccharides in the useful component obtaining step (S5).

Patent Literature 5 discloses a method of producing L-lactic acid, the method including a step of culturing lactic acid bacteria from which L-lactic acid is producible (but excluding *Enterococcus mundtii* NITEBP-965) in an environment (medium) containing, as a substrate, any one selected from the group consisting of cellobiose, cell-oligosaccharide, xylose, arabinose, and glucose that are derived from cellulose and/or hemicellulose, thereby obtaining L-lactic acid.

Patent Literature 6 discloses liquid-containing solid treatment equipment, in which a liquid-containing solid discharged through a treatment passage of a treatment apparatus is fed through piping to a solid-liquid separator where solid-liquid separation is performed. The treatment equipment is characterized by being configured to supply part of a liquid generated by the solid-liquid separation into the treatment passage of the treatment apparatus. In the case of hydrolyzing biomass under a high temperature and a high pressure to continuously obtain a saccharified solution, generally speaking, a continuous reactor including therein conveying means such as a screw feeder is used. Patent Literature 6 uses such a continuous reactor.

Patent Literature 7 discloses a biomass treatment apparatus similar to the treatment equipment of Patent Literature 6. In the biomass treatment apparatus of Patent Literature 7, water or a saccharified solution is sprayed in a reactor, and thereby carbonization of a raw material and blockage caused by carbide are reduced.

Patent Literature 8 discloses a method of and an apparatus for hydrolytically saccharifying cellulosic biomass. In the method and the apparatus, high-temperature and high-pressure slurry taken out of a pressure container is flash-evaporated in order to prevent excessive hydrolysis of a saccharified solution.

CITATION LIST

Patent Literature

PTL 1: Japanese Laid-Open Patent Application Publication No. 2000-186102
PTL 2: Japanese Laid-Open Patent Application Publication No. 2002-59118
PTL 3: Japanese Laid-Open Patent Application Publication No. 2003-212888
PTL 4: Japanese Laid-Open Patent Application Publication No. 2010-81855
PTL 5: Japanese Laid-Open Patent Application Publication No. 2013-165719
PTL 6: Japanese Laid-Open Patent Application Publication No. 2006-68606
PTL 7: Japanese Laid-Open Patent Application Publication No. 2012-22
PTL 8: (PCT) International Publication No. WO 2008/050740

SUMMARY OF INVENTION

Technical Problem

In the case of hydrolyzing cellulosic biomass into saccharides by using supercritical water or subcritical water, energy efficiency increases in accordance with an increase in the biomass concentration (solid concentration) of cellulosic biomass slurry that is to be treated hydrothermally, because the amount of biomass that can be heated with the same energy increases in accordance with an increase in the biomass concentration. In addition, the concentration load at the time of concentrating a saccharified solution that is to be used in a fermentation step can be reduced if the biomass concentration is high, because the concentration of the saccharified solution increases in accordance with an increase in the biomass concentration. Usually, the solid concentration of the biomass slurry is adjusted to fall within 5 to 10 mass %.

However, if the solid concentration of the cellulosic biomass slurry is increased in order to increase the energy efficiency, the fluidity of the slurry decreases, which makes it difficult to convey the slurry by using piping. This is a major obstacle for continuously hydrolyzing the biomass slurry by using a continuous reactor. Moreover, if the biomass concentration of the cellulosic biomass slurry is increased, thermal conductivity at an indirect heat exchanger decreases, which is another problem.

In the case of hydrothermally treating biomass slurry continuously by using a continuous reactor, it is necessary to sufficiently heat the biomass slurry by sufficiently stirring the slurry with high-temperature steam, and also, it is necessary to move the heated slurry inside the reactor as a plug flow in order to keep the hydrothermal treatment time constant. In the case of increasing the concentration of the biomass slurry, it is necessary to increase the stirring intensity compared to conventional art. However, if the stirring intensity is simply increased, the plug flow will be lost. As a result, the biomass slurry that is unreacted or saccharide hydrolysates produced from excessive hydrolysis are discharged to the outlet of the continuous reactor. Consequently, the saccharification rate decreases.

In the treatment equipment disclosed in Patent Literature 6, a saccharified solution is mixed into slurry at the outlet of the reactor. Accordingly, blockage at the outlet of the reactor can be prevented. However, the treatment equipment includes no configuration for allowing high-concentration biomass slurry to form a plug flow inside the reactor. The treatment apparatus disclosed in Patent Literature 7 also includes no configuration for allowing high-concentration biomass slurry to form a plug flow inside the reactor.

The high-temperature and high-pressure biomass slurry, after being taken out of the reactor, needs to be immediately cooled down to a temperature equal to or lower than the subcritical state, otherwise the saccharides will be excessively hydrolyzed into organic acid, and thereby the yield of the saccharides will decrease. The hydrolytic saccharification method and the hydrolytic saccharification apparatus disclosed in Patent Literature 8 are of a batch type. However, the inventors of the present invention have found out that in a case where the solid concentration of the cellulosic biomass slurry is increased, a pressure reducing valve disposed at the inlet of a flash tank tends to become clogged. Thus, increasing the solid concentration of the cellulosic biomass slurry causes a problem also in the case of cooling down the high-temperature and high-pressure slurry by flash evaporation. Patent Literatures 6 and 7 do not disclose the cooling of the high-temperature and high-pressure slurry by flash evaporation.

An object of the present invention is to provide a method of producing a saccharified solution, in which saccharified slurry is obtained by hydrothermally treating cellulosic biomass slurry in a supercritical state or a subcritical state by a continuous reactor. The method, while keeping uniform mixing of the slurry with respect to a cross section perpendicular to a mixing axis and keeping a plug flow in the axial direction, reduces the risk of a pressure reducing valve becoming clogged when the high-temperature and high-pressure slurry is flash-evaporated after being hydrothermally treated. Another object of the present invention is to provide an apparatus for producing a saccharified solution, the apparatus being suitable for executing the saccharified solution producing method.

Solution to Problem

A certain temperature (supercritical state or subcritical state) and moisture are necessary for a saccharification reaction of biomass slurry, and the saccharification reaction requires intense mixing of a crushed biomass raw material, steam, and moisture. In the case of increasing the solid concentration of the biomass slurry, more intense stirring is necessary.

In order to solve the above-described problems, the inventors of the present invention conducted diligent studies. As a result of the studies, they paid attention to the fact that in a case where cellulosic biomass slurry whose solid concentration has been adjusted to be not less than 15 mass % and not more than 50 mass % is hydrothermally treated in a supercritical state or a subcritical state, part of the biomass becomes solubilized as the saccharification reaction progresses, and thereby the viscosity of the slurry decreases. The inventors of the present invention also took notice of the following fact: by crushing solid matter contained in saccharified slurry (i.e., solid matter such as an adhering material formed in the continuous reactor) whose solid concentration is higher than in conventional art by a crushing apparatus such as a cutter pump into pieces, the risk of the pressure reducing valve becoming clogged is reduced even if the saccharified slurry is flash-evaporated. As a result, the inventors of the present invention arrived at the present invention.

Specifically, the present invention relates to a method of producing a saccharified solution by using biomass as a raw material, the method including: a hydrolytic saccharification step of obtaining saccharified slurry by hydrothermally treating cellulosic biomass slurry in a supercritical state or a subcritical state by a continuous reactor; a crushing step of supplying the saccharified slurry that is taken out of the continuous reactor to a crushing apparatus, and crushing solid matter formed in the continuous reactor by the crushing apparatus; a flash step of flash-evaporating and cooling down, in a flash tank through a pressure reducing valve, the saccharified slurry that is taken out of the crushing apparatus; and a solid-liquid separation step of performing solid-liquid separation to separate the slurry that is taken out of the flash tank into a saccharified solution and solid matter.

The present invention also relates to an apparatus for producing a saccharified solution by using biomass as a raw material, the apparatus including: a continuous reactor that hydrothermally treats cellulosic biomass slurry in a supercritical state or a subcritical state; a crushing apparatus that crushes solid matter formed in the continuous reactor, the solid matter being contained in saccharified slurry that is taken out of the continuous reactor; a flash tank that flash-evaporates, through a pressure reducing valve, the saccharified slurry that is taken out of the crushing apparatus; a solid-liquid separator that performs solid-liquid separation to separate the slurry that is taken out of the flash tank into a saccharified solution and solid matter; and saccharified slurry supply piping that supplies the saccharified slurry that is taken out of the continuous reactor to the crushing apparatus.

A first feature of the present invention is to hydrothermally treating the cellulosic biomass slurry in a supercritical state or a subcritical state by using the continuous reactor, which includes a front part and a rear part, the front part mixing the cellulosic biomass slurry and steam, the rear part moving the slurry mixed with the steam toward an outlet as a plug flow in an axial direction while uniformly mixing the slurry with respect to a cross section perpendicular to a mixing axis.

Preferably, in the crushing step, part of the saccharified solution that is obtained in the solid-liquid separation step is added to the saccharified slurry to dilute the saccharified slurry.

Preferably, the apparatus for producing a saccharified solution further includes saccharified solution supply piping that supplies part of the saccharified solution that is taken out of the solid-liquid separator to the crushing apparatus. Preferably, the crushing apparatus mixes the saccharified slurry that is taken out of the continuous reactor and the saccharified solution, and crushes solid matter contained in the saccharified slurry that has been diluted with the saccharified solution.

By diluting the saccharified slurry with the saccharified solution, the solid matter can be readily crushed by the crushing apparatus, and the risk of clogging of the pressure reducing valve at the time of flash evaporation is further reduced.

Preferably, the continuous reactor includes: a front part including biaxial screws, biaxial paddles, biaxial oval blades, or biaxial kneaders, the front part mixing the cellulosic biomass slurry and steam; and a rear part including pin vanes or plate vanes, the rear part moving the slurry mixed with the steam toward an outlet as a plug flow in an axial direction while uniformly mixing the slurry with respect to a cross section perpendicular to a mixing axis.

In the front part, the biomass raw material that has been crushed, steam, and moisture are intensely mixed together by the biaxial screws, the biaxial paddles, the biaxial oval blades, or the biaxial kneaders. In the rear part where the viscosity of the slurry decreases as the hydrolysis progresses, if intense mixing as in the front part is performed, the plug flow of the slurry cannot be kept. Therefore, mixing is performed gently in the rear part by the pin vanes or the plate vanes. It is practical to form the front part such that the front part constitutes ¼ to ½ of the inlet side of the continuous reactor. The first feature of the present invention makes it possible to sufficiently stir the biomass slurry and the steam, and in the rear part of the reactor, keep the plug flow in the axial direction while uniformly mixing the slurry and the steam with respect to the cross section perpendicular to the mixing axis.

A second feature of the present invention is to: dilute the high-temperature and high-pressure slurry by using part of the saccharified solution obtained in the solid-liquid separation step to reduce the viscosity; crush solid matter contained in the slurry (i.e., solid matter such as an adhering material formed in the continuous reactor) by the crushing apparatus such as a cutter pump; and thereafter supply the high-temperature and high-pressure slurry to the flash tank to flash-evaporate and quickly cool down the slurry.

In the case of supplying the high-temperature and high-pressure saccharified slurry to the flash tank to flash-evaporate the slurry, the pressure reducing valve at the inlet of the flash tank tends to become clogged with solid matter. In this respect, if the solid concentration of the saccharified slurry is higher than in conventional art, the pressure reducing valve is more likely to become clogged with the solid matter. Therefore, the high-temperature and high-pressure slurry that is taken out of the continuous reactor, and part of the saccharified solution that is obtained in the solid-liquid separation step after the saccharified slurry is cooled down, are supplied to the crushing apparatus, and thereby the saccharified slurry is diluted and the viscosity thereof is reduced. In addition, the diluted saccharified slurry is further crushed into pieces by the crushing apparatus. As a result, clogging of the pressure reducing valve due to the flash evaporation of the diluted saccharified slurry can be prevented.

Preferably, the crushing apparatus includes: a mixing chamber including a stirring device that mixes the saccharified slurry and the saccharified solution; a crushing blade for crushing solid matter contained in the saccharified slurry that has been diluted with the saccharified solution; and a screen that separates the solid matter. Preferably, the saccharified slurry supply piping and the saccharified solution supply piping are connected to the mixing chamber, and the crushing apparatus supplies the saccharified slurry that has passed through the screen and that has been diluted to outside.

By using the crushing apparatus with the above-described structure, solid matter contained in the saccharified slurry can be crushed by the crushing blade, and the saccharified slurry that has been crushed to such an extent that the solid matter therein can pass through the screen can be supplied to the flash tank.

The present invention further relates to a continuous reactor for hydrothermally treating cellulosic biomass slurry in a supercritical state or a subcritical state, the continuous reactor including: a front part including biaxial screws, biaxial paddles, biaxial oval blades, or biaxial kneaders, the front part mixing the cellulosic biomass slurry and steam; and a rear part including pin vanes or plate vanes, the rear part moving the slurry mixed with the steam toward an outlet as a plug flow in an axial direction while uniformly mixing the slurry with respect to a cross section perpendicular to a mixing axis.

Preferably, the front part constitutes ¼ to ½ of an inlet side of the continuous reactor.

In the continuous reactor according to the present invention, preferably, the biaxial screws, the biaxial paddles, the biaxial oval blades, or the biaxial kneaders of the front part, and the pin vanes or the plate vanes of the rear part, are provided on the same rotary shaft(s).

Preferably, the continuous reactor according to the present invention includes two rotary shafts that are parallel to each other.

Advantageous Effects of Invention

According to the present invention, the cellulosic biomass slurry can be hydrothermally treated by the continuous reactor continuously in a stable manner, and even if the saccharified slurry is quickly cooled down by flash evaporation, the pressure reducing valve is less likely to become clogged. In the present invention, cellulosic biomass slurry whose solid concentration has been adjusted to be not less than 15 mass % and not more than 50 mass % is treatable.

DESCRIPTION OF EMBODIMENTS

Hereinafter, one embodiment of the present invention is described with reference to the drawings. The present invention is not limited to the embodiment described below.

Comparative Example 1/Preliminary Test

Figure 1:
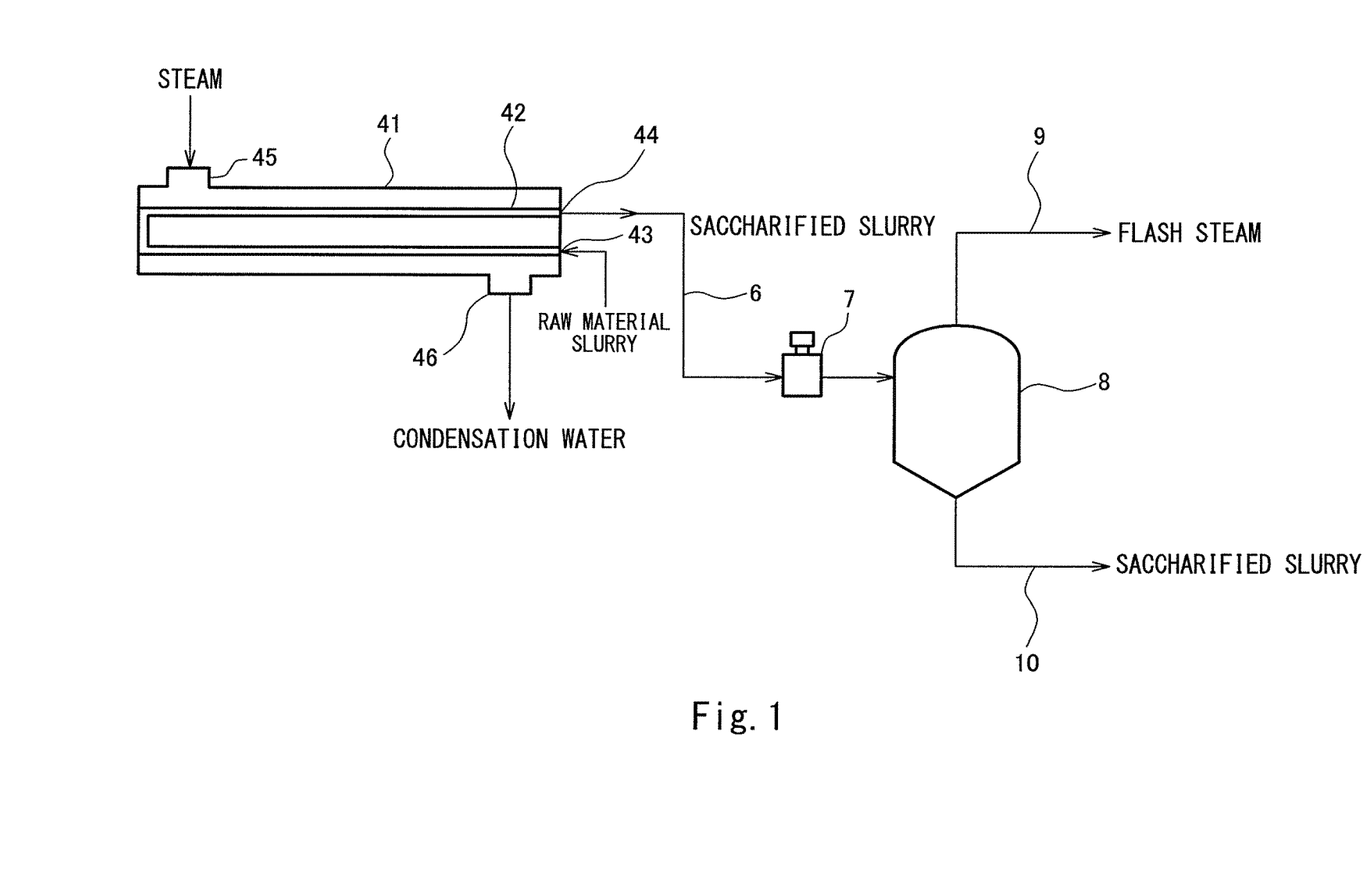
FIG. 1 is a schematic diagram showing a saccharified solution producing apparatus of Comparative Example 1.

Rice straw was used as cellulosic biomass. First, the rice straw was ground by a grinder to have a median diameter of 100 to 200 μm. Water was added and mixed with the ground rice straw, and thereby biomass raw material slurry with a solid concentration of 7 mass % was prepared. The raw material slurry was supplied to an inlet 43 of an indirect heating shell-and-tube reactor 41 (manufactured by Kawasaki Heavy Industries, Ltd.) by using a high pressure pump. The temperature and pressure inside the indirect heating shell-and-tube reactor 41 were adjusted to a temperature of 180° C. and a pressure of 2 MPa. FIG. 1 is a schematic diagram showing a saccharified solution producing apparatus of Comparative Example 1. Although a slurry heating tube 42 is provided inside the indirect heating shell-and-tube reactor 41, no stirring device is provided inside the reactor 41. The slurry that had been saccharified was taken out of an outlet 44 of the indirect heating shell-and-tube reactor 41, and was supplied to a flash tank 8 through a passage 6 and a pressure reducing valve 7.

After 24 hours had elapsed since the start of the test, pressure loss in the reactor increased gradually. Then, after 72 hours had elapsed since the start of the test, it became difficult for the reactor to continue operating. At the time, the operation was stopped, and the reactor was opened and inspected. It was confirmed in the inspection that blockage had occurred inside the reactor due to deposits. Substantially the same results were obtained also in a case where the solid concentration of the raw material slurry was adjusted to 3 mass %.

Based on the above, it has been concluded that stirring means (a stirrer) for removing the deposits is necessary inside the reactor, and a crusher for crushing the deposits (i.e., solidified materials formed when solid matter contained in the raw material slurry is scorched) that have detached from the reactor is necessary at the outlet side or downstream side of the reactor. It has also been concluded that the above configuration is even more necessary in the case of increasing the solid concentration of the raw material slurry compared to conventional art.

Working Example

The same rice straw as that used in the preliminary test was used to prepare raw material slurry whose solid concentration was 30 mass %. With use of the raw material slurry, a saccharified solution was produced by a saccharified solution producing apparatus shown in FIG. 2. The raw material slurry was supplied to an inlet 2 of a continuous reactor 21. Steam was also supplied to the inlet 2 of the continuous reactor 21, and used for heating the raw material slurry.

Figure 2:
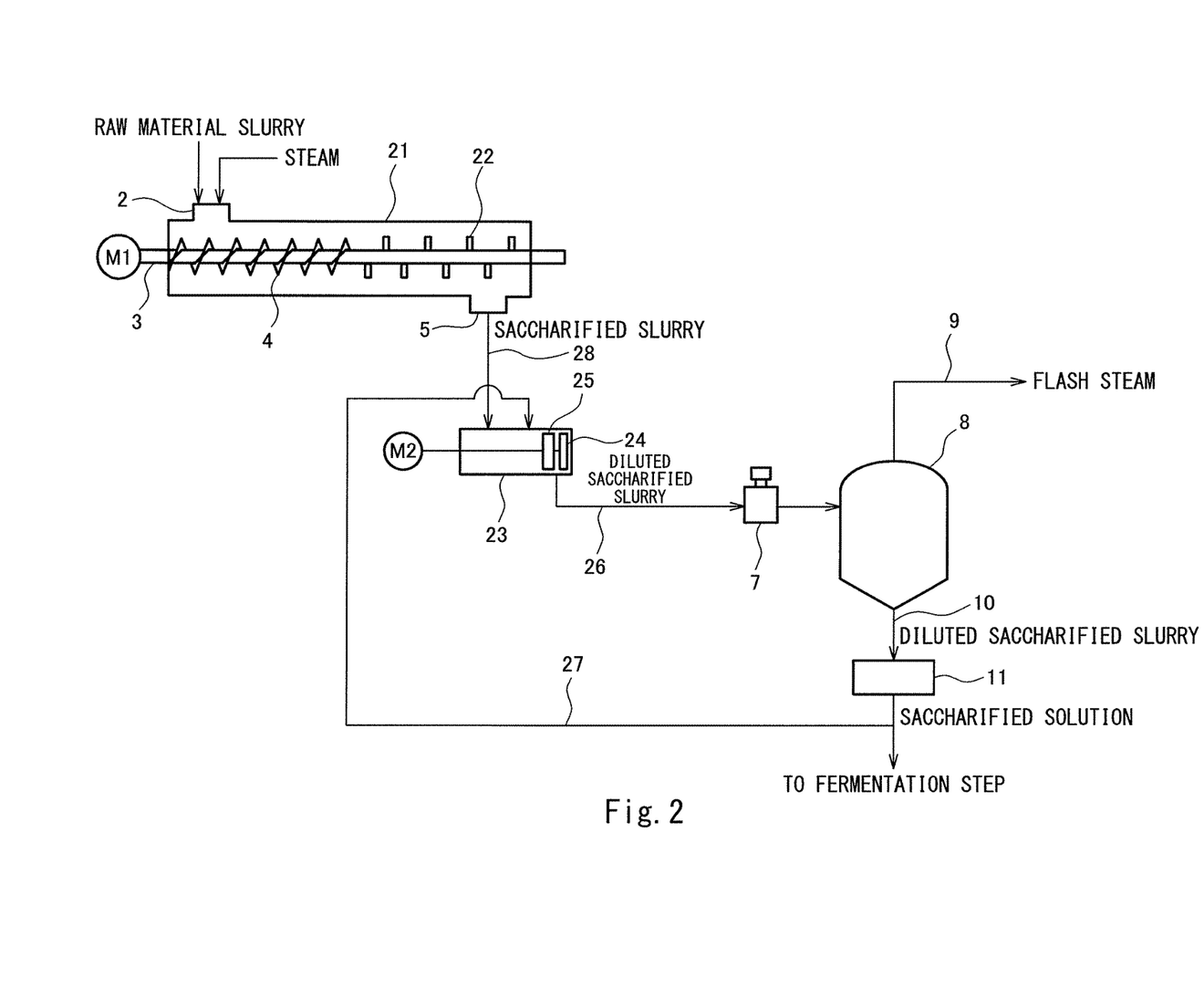
FIG. 2 is a schematic diagram showing a saccharified solution producing apparatus of a working example.

The continuous reactor 21 includes therein two types of stirring devices. Rotary shafts 3 of these stirring devices are driven by a motor M1. A stirring device 4, which is a front stirring device, is formed by screws, paddles, oval blades, or kneaders. A stirring device 22, which is a rear stirring device, is formed by pin vanes or plate vanes. FIG. 2 shows only one rotary shaft. However, in fact, two rotary shafts are provided parallel to each other horizontally, and each of the rotary shafts is provided with the stirring device 4 and the stirring device 22. That is, both the stirring device 4 and the stirring device 22 shown in FIG. 2 are of a biaxial type.

The raw material slurry that is fed through the inlet 2 of the continuous reactor 21 is intensely mixed with the steam by the front stirring device 4, and is moved toward an outlet 5 (to the right in FIG. 2) while the raw material slurry is being heated to a predetermined temperature and pressurized. After the raw material slurry has become high-temperature and high-pressure slurry, while the raw material slurry is being moved to the rear part of the continuous reactor 21, part of cellulose or hemicellulose contained in the slurry is hydrolyzed into saccharides, and the viscosity of the slurry decreases (i.e., saccharified slurry). If it is attempted to convey the saccharified slurry to the outlet 5 by the stirring device 4, the saccharified slurry near the stirring device 4 moves forward to the outlet 5, but the saccharified slurry near the inner wall of the continuous reactor 21, i.e., the saccharified slurry away from the stirring device 4, moves backward. Consequently, the plug flow of the saccharified slurry will be lost.

When the plug flow is thus lost, the hydrothermal treatment time of the saccharified slurry near the stirring device 4 becomes shorter than a predetermined time, and the hydrolysis of the cellulose or hemicellulose into saccharides becomes insufficient. On the other hand, the hydrothermal treatment time of the saccharified slurry near the reaction container inner wall becomes longer than the predetermined time, and saccharides obtained from hydrolyzing the cellulose or hemicellulose are excessively hydrolyzed into hydrolysates, such as organic acid.

Accordingly, the continuous reactor 21 is provided with the pin vanes or plate vanes serving as the rear stirring device 22. In a case where pin vanes or plate vanes serve as the rear stirring device 22, the force of propelling the stirred material is less than in a case where screws, paddles, oval blades, or kneaders serve as the rear stirring device 22. Therefore, in this case, even if the rotation speed of the rotary shafts is increased by the motor M1 in order to intensely mix the raw material slurry and the steam by the front stirring device 4, the plug flow of the saccharified slurry is less likely to be lost. As a result, the following advantages can be obtained: the hydrothermal treatment time of the saccharified slurry conveyed through the rear part of the continuous reactor 21 can be readily controlled; and the saccharification yield can be improved. Preferably, the peripheral speed of the rear stirring device 22 is adjusted to be 0.5 m/sec or higher.

The high-temperature and high-pressure saccharified slurry that is taken out of the outlet 5 of the continuous reactor 21 often contains deposits that have detached from the reactor. In addition, the higher the solid concentration of the raw material slurry, the higher the solid concentration and viscosity of the saccharified slurry. Accordingly, if it is attempted to directly supply the saccharified slurry to the flash tank 8 and flash-evaporate the saccharified slurry, the pressure reducing valve 7 (usually an angle valve) tends to become clogged with the deposits and/or solid matter. Therefore, in the present invention, preferably, part of a saccharified solution that is obtained from saccharified slurry solid-liquid separation at a subsequent stage is mixed into the saccharified slurry to dilute the saccharified slurry for further reduction of its viscosity, and then solid matter contained in the diluted saccharified slurry is crushed into pieces by using a crushing apparatus 23.

Figure 3:
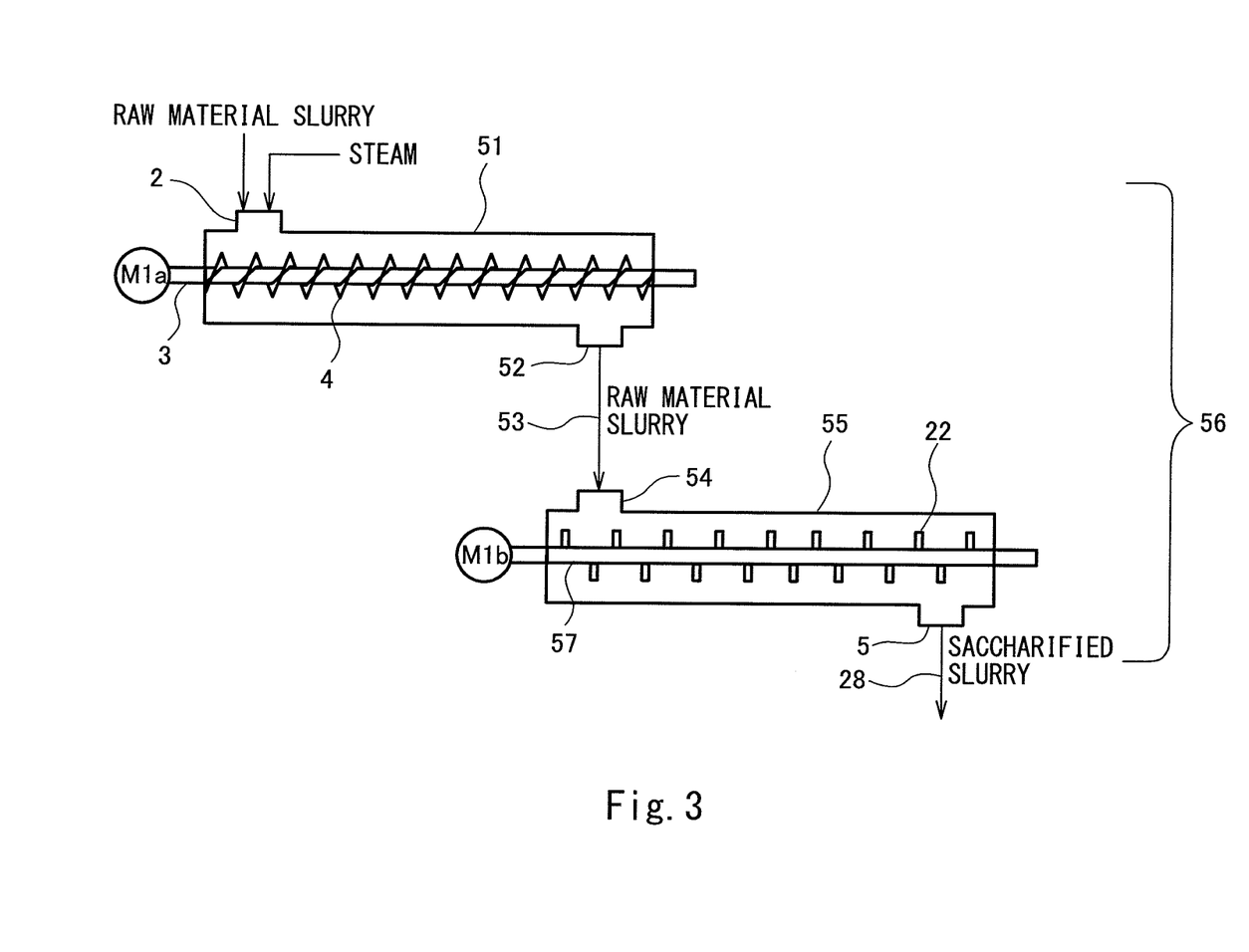
FIG. 3 shows another example of a continuous reactor.

FIG. 3 shows another example of the structure of the continuous reactor. In the case of increasing the required capacity of the continuous reactor, it is preferable to adopt a structure in which a front part 51 and a rear part 55 are separately provided. In FIG. 3, each of the front part 51 including the stirring device 4 and the rear part 55 including the stirring device 22 is an independent casing, and these front and rear parts 51 and 55 form a continuous reactor 56. The rotary shafts 3 of the stirring device 4 are driven by a motor M1a, and a rotary shaft/shafts 57 of the stirring device 22 is/are driven by a motor M1b.

The functions of the front part 51 and the rear part 55 are the same as those of the front part and the rear part of the continuous reactor 21 shown in FIG. 2. The raw material slurry fed through the inlet 2 of the front part 51 is intensely mixed with steam by the stirring device 4, and is moved to an outlet 52 while the raw material slurry is being heated to a predetermined temperature and pressurized. The raw material slurry that has become high-temperature and high-pressure slurry is supplied to an inlet 54 of the rear part 55 through a transfer passage 53. The transfer passage 53 is a closed line.

In the continuous reactor 56, it is preferred that the inner volume of the rear part 55 be greater than the inner volume of the front part 51. The stirring device 22 of the rear part 55 may be of a biaxial type or a monoaxial type.

Figure 4:
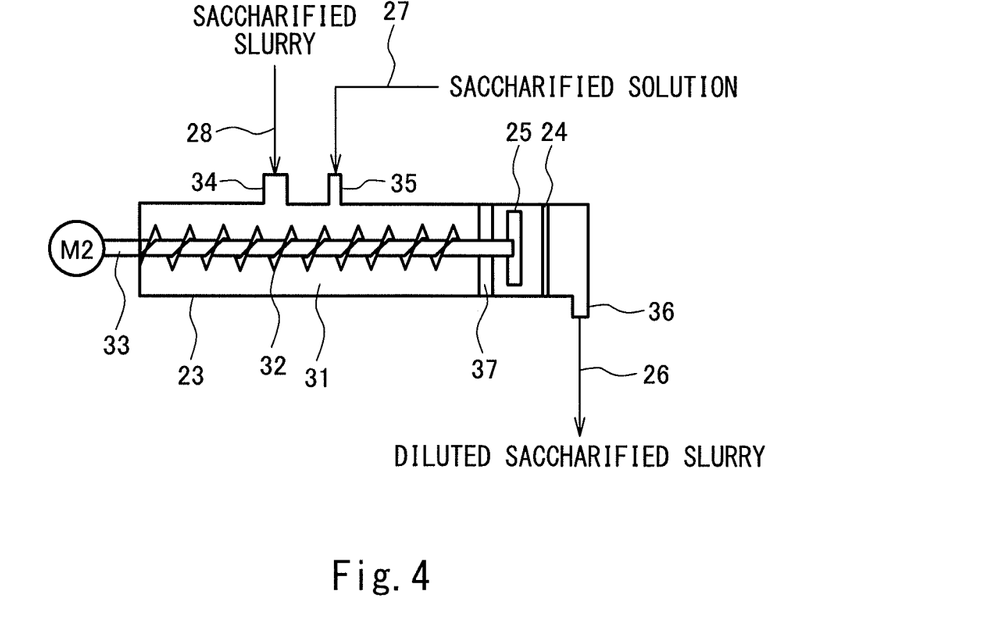
FIG. 4 is a schematic diagram showing one example of a crushing apparatus.

FIG. 4 is a schematic diagram showing one example of the crushing apparatus 23. The crushing apparatus 23 includes a mixing chamber 31, a crushing blade 25, and a screen 24. The mixing chamber 31 includes a stirring device 32. A rotary shaft 33 of the stirring device 32 is driven by a motor M2. The crushing blade 25 is also connected to the rotary shaft 33. Saccharified slurry supply piping 28 is connected to a saccharified slurry inlet 34, and the saccharified slurry that is taken out of the outlet 5 of the continuous reactor 21 is supplied to the saccharified slurry inlet 34. Saccharified solution supply piping 27 is connected to a saccharified solution inlet 35, and part of a saccharified solution that is obtained from a solid-liquid separator described below is supplied to the saccharified solution inlet 35. The saccharified slurry inlet 34 and the saccharified solution inlet 35 may be integrated together.

The saccharified slurry and the saccharified solution supplied to the mixing chamber 31 are stirred together by the stirring device 32, and thereby the saccharified slurry is diluted. Preferably, the stirring device 32 is a screw or paddles. The diluted saccharified slurry circulates between the mixing chamber 31 and the screen 24 while its solid matter is being crushed by the crushing blade 25. Preferably, the crushing blade 25 is cutter-shaped or has a shape similar to that of a stone mill. By setting the clearance between the crushing blade 25 and the screen 24 to be in the range of 0.05 to 0.5 mm, the screen 24 may be allowed to double as a fixed blade.

The diluted saccharified slurry whose solid matter has been sufficiently crushed so that the slurry can pass through the screen 24 is taken out of an outlet 36 to a passage 26. The screen 24 is made of a metal such as stainless steel, and the diameter of each opening of the mesh screen is preferably 1 to 5 mm.

The diluted saccharified slurry taken out to the passage 26 is supplied to the flash tank 8 through the pressure reducing valve 7. Here, the diluted saccharified slurry is flash-evaporated in the flash tank and quickly cooled down to a temperature at which excessive hydrolysis of saccharides does not occur. In the present invention, preferably, the saccharified slurry that is to be flash-evaporated is diluted with the saccharified solution so that the saccharide concentration of the saccharified slurry will not be reduced, and the solid matter contained in the saccharified slurry is crushed by the crushing apparatus 23. By diluting the saccharified slurry by the saccharified solution, even if the solid concentration of the raw material slurry is higher than in conventional art, the pressure reducing valve 7 is less likely to become clogged with the solid matter.

Flash steam is taken out to a flash passage 9, and its heat is recovered as necessary. The saccharified slurry that has been cooled down is taken out to a passage 10, and is supplied to a solid-liquid separator 11 through the passage 10. Examples of the solid-liquid separator 11 include a decanter, a drum filter, a belt filter, a disc filter, and a filter press. The resulting saccharified solution is supplied to a concentrator, such as a reverse osmosis membrane device or a distillation device, as necessary. After the saccharide concentration is increased by the concentrator, the saccharified solution is supplied to a fermentation apparatus where a fermentation step, such as alcoholic fermentation or lactic acid fermentation, is performed.

Here, part of the saccharified solution that is taken out of the solid-liquid separator 11 is, as mentioned above, supplied to the saccharified solution inlet 35 of the crushing apparatus 23 through the saccharified solution supply piping 27. Since the saccharified solution is used as a diluent for the saccharified slurry, even when the saccharified slurry is diluted, the saccharide concentration thereof is not reduced, and an increase in the load on the concentrator (in the concentration step) can be suppressed. At the start of the operation, there is no saccharified solution that can be used for diluting the saccharified slurry. In this case, preferably, not water but a saccharide aqueous solution suitable for use in the fermentation step is used as a diluent.

The raw material slurry that had been prepared and steam (200° C., 1.45 MPa) were supplied (a supply amount of 235 kg/hour) to the continuous reactor (having a total volume of 200 L and an effective volume of 90 L), and the inside of the reactor was kept to 165° C. and 0.9 MPa. The front stirring device of the continuous reactor was formed by 46 paddles, and the rear stirring device was formed by 80 pin vanes. The peripheral speed of each stirring device was 0.7 m/sec. The solid concentration of the raw material slurry after being mixed with the steam was adjusted to 25 mass %. Under these conditions, uniform mixing of the raw material slurry (saccharified slurry) with respect to a cross section perpendicular to a mixing axis and a plug flow in the axial direction were stably kept for 24 hours or longer without spraying water or saccharified solution in the continuous reactor, and neither carbonization of the raw material slurry nor blockage due to carbide was observed. The saccharification rate was 70% of the planned value.

The saccharified slurry that had been taken out of the continuous reactor was supplied (a supply amount of 1175 kg/hour) to the crushing apparatus including: the mixing chamber with a volume of 3 L; an impeller serving as the crushing blade, the impeller including four cutters; paddles serving as the stirring device; and the screen with a mesh opening diameter of 3 mm. The saccharified slurry was mixed with the saccharified solution whose amount was five times as great as the amount of the saccharified slurry. The rotation speed of the motor M2 was set to 100 rpm. The diluted saccharified slurry that had been taken out of the crushing apparatus was supplied to the flash tank having an inner volume of 1.8 m$^3$ through the pressure reducing valve (angle valve, piping connection 25A), and was flash-evaporated. Under these conditions, no blockage of the pressure reducing valve was observed even after the elapse of 24 hours.

Comparative Example 2

Figure 5:
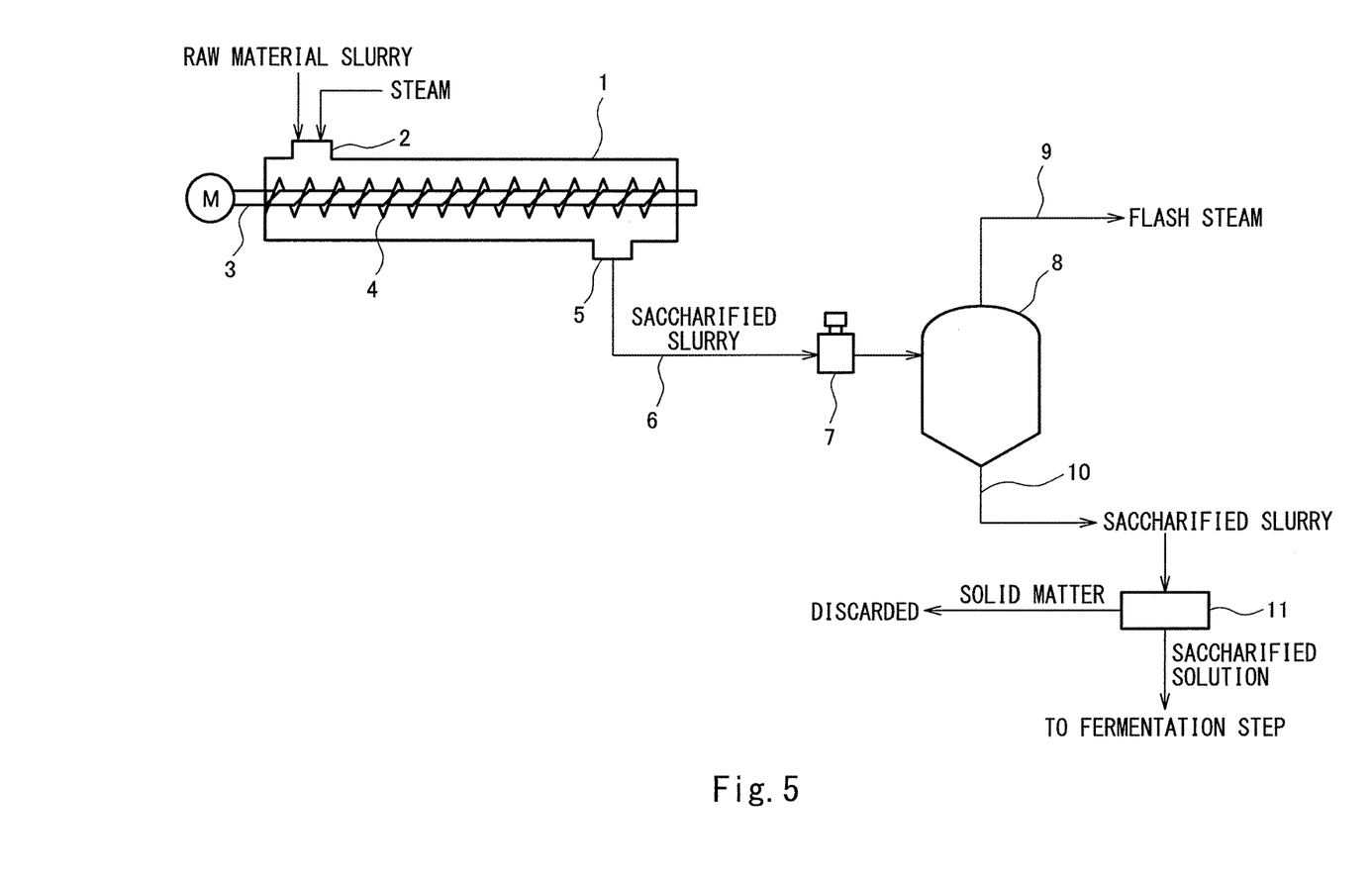
FIG. 5 is a schematic diagram showing a saccharified solution producing apparatus of Comparative Example 2.

A continuous reactor 1 of a saccharified solution producing apparatus shown in FIG. 5 is an ordinary reactor including biaxial screws as the stirring device 4, and the rotary shafts 3 of the continuous reactor 1 are driven by a motor M. The dimensions of the continuous reactor 1 are the same as those of the continuous reactor 21 used in the working example.

A tracer test was performed, in which a simulation liquid simulating the raw material slurry and a staining liquid were supplied to, and mixed together in, the continuous reactor 1 at a normal temperature with no steam supplied thereto. It was confirmed in the test that, owing to the stirring device 4, the reactor was in the state of complete mixing tank, and that the plug flow was lost.

Comparative Example 3

The operation was performed in the same manner as in the working example except that the crushing apparatus 23 was not used and the saccharified slurry was not diluted with the saccharified solution. Glucose was intermittently fed during steady operation, and flow analysis of the inside of the continuous reactor 21 was conducted. As a result, a plug flow corresponding to four tanks in terms of the complete mixing row model was kept, and the saccharification rate reached 70% of the planned value.

However, in the case of continuous operation for 24 hours or longer, the pressure reducing valve 7 was clogged up frequently, causing serious troubles for practical use.

INDUSTRIAL APPLICABILITY

The method of and the apparatus for producing a saccharified solution by using biomass as a raw material, and the continuous reactor, according to the present invention are useful in the fields of bioenergy and biochemicals as a method of and an apparatus for producing a saccharified solution by hydrolyzing cellulosic biomass.

REFERENCE SIGNS LIST 1, 21: continuous reactor
2: inlet of continuous reactor (feeding port)
3, 33: rotary shaft
4: stirring device (screw)
5: outlet of continuous reactor (take-out port)
6, 10, 26: passage
7: pressure reducing valve
8: flash tank
9: flash passage
11: solid-liquid separator
22: stirring device (pin vane)
23: crushing apparatus
24: screen
25: crushing blade
27: saccharified solution supply piping
28: saccharified slurry supply piping
31: mixing chamber
32: stirring device
34: saccharified slurry inlet
35: saccharified solution inlet
36: outlet of crushing apparatus
37: rotary shaft supporting member
41: indirect heating shell-and-tube reactor
42: raw material slurry heating tube
43: inlet of indirect heating shell-and-tube reactor (feeding port)
44: outlet of indirect heating shell-and-tube reactor (take-out port)
45: steam inlet
46: condensation water outlet 51: front part
52: outlet of front part
53: transfer passage
54: inlet of rear part
55: rear part
56: continuous reactor
57: rotary shaft
M, M1, M1a, M1b, M2: motor

The invention claimed is:

1. A method of producing a saccharified solution by using biomass as a raw material, the method comprising:
  a hydrolytic saccharification step comprising hydrothermally treating a cellulosic biomass slurry in a supercritical state or a subcritical state in a continuous reactor to obtain a saccharified slurry containing solid materials formed in the continuous reactor, the continuous reactor having a front part configured to mix the cellulosic biomass slurry and steam and a rear part configured to move the slurry mixed with the steam toward an outlet as a plug flow in an axial direction of the continuous reactor;
  a crushing step comprising supplying the saccharified slurry to a crushing apparatus, and then crushing the solid materials in the saccharified slurry into pieces with the crushing apparatus;
  a flash step comprising supplying the saccharified slurry, containing the crushed solid materials, through a pressure reducing valve to a flash tank, and then flash-evaporating and cooling down the saccharified slurry; and
  a solid-liquid separation step of performing solid-liquid separation to separate the cooled down saccharified slurry into a saccharified solution and solid matter.

2. The method of producing a saccharified solution according to claim 1, wherein
  in the crushing step, part of the saccharified solution that is obtained in the solid-liquid separation step is added to the saccharified slurry to dilute the saccharified slurry.

3. The method of producing a saccharified solution according to claim 1, wherein
  the front part includes biaxial screws, biaxial paddles, biaxial oval blades, or biaxial kneaders,
  the rear part includes pin vanes or plate vanes, and
  the biaxial screws, the biaxial paddles, the biaxial oval blades, or the biaxial kneaders of the front part, and the pin vanes or the plate vanes of the rear part, are provided on a same rotary shaft or same rotary shafts.

4. An apparatus for producing a saccharified solution by using biomass as a raw material, the apparatus comprising:
  a continuous reactor configured to hydrothermally treat a cellulosic biomass slurry in a supercritical state or a subcritical state to obtain a saccharified slurry containing solid materials formed in the continuous reactor, the continuous reactor having a front part configured to mix the cellulosic biomass slurry and steam and a rear part configured to move the slurry mixed with the steam toward an outlet as a plug flow in an axial direction of the continuous reactor;
  a crushing apparatus configured to crush the solid materials contained in the saccharified slurry into pieces;
  a flash tank configured to flash-evaporate and cool down the saccharified slurry containing the crushed solid materials;
  a pressure reducing valve disposed at an inlet of the flash tank, and through which the saccharified slurry containing the crushed solid materials is supplied to the flash tank;
  a solid-liquid separator configured to perform solid-liquid separation to separate the cooled down saccharified slurry into a saccharified solution and solid matter; and
  saccharified slurry supply piping configured to supply the saccharified slurry from the continuous reactor to the crushing apparatus.

5. The apparatus for producing a saccharified solution according to claim 4, further comprising:
  saccharified solution supply piping configured to supply part of the saccharified solution from the solid-liquid separator to the crushing apparatus,
  wherein the crushing apparatus is configured to mix the saccharified slurry containing the solid materials with the saccharified solution, and to crush the solid materials contained in the saccharified slurry that has been diluted with the saccharified solution.

6. The apparatus for producing a saccharified solution according to claim 4, wherein
  the front part includes biaxial screws, biaxial paddles, biaxial oval blades, or biaxial kneaders,
  the rear part includes pin vanes or plate vanes, and
  the biaxial screws, the biaxial paddles, the biaxial oval blades, or the biaxial kneaders of the front part, and the pin vanes or the plate vanes of the rear part, are provided on a same rotary shaft or same rotary shafts.

7. The apparatus for producing a saccharified solution according to claim 5, wherein
  the crushing apparatus includes:
    a mixing chamber including a stirring device configured to mix the saccharified slurry and the saccharified solution;
    a crushing blade configured to crush the solid materials contained in the saccharified slurry that has been diluted with the saccharified solution; and
    a screen configured to separate any of the solid materials that are larger than a predetermined size,
  the saccharified slurry supply piping and the saccharified solution supply piping are connected to the mixing chamber, and
  the crushing apparatus is configured to supply the saccharified slurry that has passed through the screen and that has been diluted to outside.

8. A continuous reactor for hydrothermally treating cellulosic biomass slurry in a supercritical state or a subcritical state, the continuous reactor comprising:
  a front part including biaxial screws, biaxial paddles, biaxial oval blades, or biaxial kneaders, the front part being configured to mix the cellulosic biomass slurry and steam and forming an inlet side of the continuous reactor and constituting ¼ to ½ of the continuous reactor; and
  a rear part including pin vanes or plate vanes, the rear part being configured to move the slurry mixed with the steam toward an outlet as a plug flow in an axial direction of the continuous reactor,
  wherein the biaxial screws, the biaxial paddles, the biaxial oval blades, or the biaxial kneaders of the front part, and the pin vanes or the plate vanes of the rear part, are provided on a same rotary shaft or same rotary shafts.

9. The continuous reactor according to claim 8, comprising two rotary shafts that are parallel to each other.

* * * * *